United States Patent [19]

Miura et al.

[11] Patent Number: 4,994,456
[45] Date of Patent: Feb. 19, 1991

[54] PYRIDINECARBOXYLIC ACID AMIDE DERIVATIVES AND PHARMACEUTICAL COMPOSITIONS COMPRISING SAME

[75] Inventors: Katsutoshi Miura; Hiroyasu Koyama; Toshiji Sugai; Hiroaki Yamada; Einosuke Sakurai, all of Saitama; Masato Horigome, Tokyo, all of Japan

[73] Assignee: Nisshin Flour Milling Co., Ltd., Tokyo, Japan

[21] Appl. No.: 483,532

[22] Filed: Feb. 22, 1990

[30] Foreign Application Priority Data

Mar. 1, 1989 [JP] Japan ................................. 1-46648
Feb. 8, 1990 [JP] Japan ................................. 2-27202

[51] Int. Cl.$^5$ ................ C07D 401/04; C07D 401/06; C07D 401/14; A61K 31/495
[52] U.S. Cl. ................................. 514/218; 514/252; 540/575; 544/364; 544/365
[58] Field of Search ................ 540/575; 544/364, 365; 546/316; 514/218, 252

[56] References Cited

U.S. PATENT DOCUMENTS 4,200,640 4/1980 Nagano et al. ................ 546/316
4,514,408 4/1985 Nisato ................ 514/212

FOREIGN PATENT DOCUMENTS 2514334 10/1975 Fed. Rep. of Germany ...... 546/316
205052 9/1987 Japan ................ 546/316
286968 12/1987 Japan ................ 546/316

OTHER PUBLICATIONS

Organic Synthesis, vol. 3, 723–5.

Primary Examiner—Robert Gerstl
Attorney, Agent, or Firm—Abelman Frayne Rezac & Schwab

[57] ABSTRACT

Compounds are disclosed of the formula

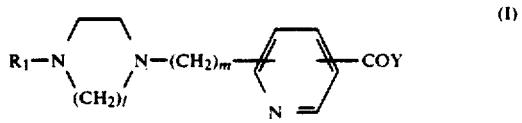
(I)

wherein
$R_1$ is hydrogen; $C_1$–$C_6$ alkyl; $C_3$–$C_6$ cycloalkyl or diphenylmethyl;
Y is —NH(CH$_2$)$_n$—R$_2$ or

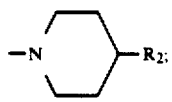

$R_2$ is OH or —ONO$_2$;
l is 2 or 3; m is 0 or 1; and n is 2 to 8; and
physiologically acceptable acid addition salts thereof. The compounds of formula (I) are of a blood flow-increasing and hypotensive actions and can be used for the therapy or prevention of diseases in the cardiovascular system.

8 Claims, No Drawings

PYRIDINECARBOXYLIC ACID AMIDE DERIVATIVES AND PHARMACEUTICAL COMPOSITIONS COMPRISING SAME

FIELD OF THE INVENTION

The present invention relates to new pyridinecarboxylic acid amide derivatives, a process for preparing the same and pharmaceutical compositions comprising said derivatives.

The pyridinecarboxylic acid amide derivatives and their physiologically acceptable salts of the invention possess an activity of increasing blood flow of vertebral, common carotid and femoral arteries and a hypotensive activity, which are effective in the therapy and prevention of disturbances of cerebral or peripheral circulation, ischemic heart diseases and hypertensions.

BACKGROUND OF THE INVENTION

Nicotinic acid amide derivatives useful as a therapeutic agent for cardiovascular diseases are disclosed in Japanese Patent Kokai No. 62-286968. Nitrate ester derivatives useful as vasodilator are also disclosed in Japanese Patent Kokai No. 62-205052. However, they are not satisfactory in efficacy as therapeutic agent for cardiovascular diseases. Thus there is a continuing need for new compounds with more improved pharmacological activities than known nicotinic acid amide derivatives.

The present invention results from efforts to develop new compounds possessing a high pharmacological activity, being readily available on an industrial scale and being satisfactory in practical use.

DISCLOSURE OF THE INVENTION

According to the invention, there are provided pyridinecarboxylic acid amide compounds of formula (I)

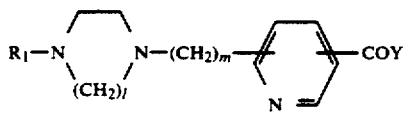

wherein
$R_1$ is hydrogen; $C_1$–$C_6$ alkyl; $C_3$–$C_6$ cycloalkyl or diphenylmethyl;
Y is $-NH(CH_2)_n-R_2$ or

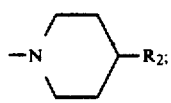

$R_2$ is OH or $-ONO_2$;
l is 2 or 3; m is 0 or 1; and n is 2 to 8; and
physiologically acceptable acid addition salts thereof.

Examples of $R_1$ in formula (I) include hydrogen; $C_1$–$C_6$ alkyl such as methyl, ethyl, n-propyl, i-propyl, n-butyl, i-butyl, tert-butyl, hexyl; $C_3$–$C_6$ cycloalkyl such as cyclopentyl and cyclohexyl; and diphenylmethyl.

Representative examples of the compounds according to the invention are as follows:
(1) N-(2-Hydroxyethyl)-6-(4-methyl-1-piperazinyl)-nicotinamide,
(2) N-(2-Hydroxyethyl)-6-(1-piperazinyl)nicotinamide,
(3) N-(2-Hydroxyethyl)-6-(4-diphenylmethyl-1-piperazinyl)nicotinamide,
(4) N-(2-Hydroxyethyl)-6-(4-ethyl-1-piperazinyl)-nicotinamide,
(5) N-(2-Hydroxyethyl)-6-(4-cyclopentyl-1-piperazinyl)nicotinamide,
(6) N-(2-Hydroxyethyl)-6-(4-methyl-1-homopiperazinyl)nicotinamide,
(7) N-(2-Hydroxyethyl)-2-(4-methyl-1-piperazinyl)-nicotinamide,
(8) N-(2-Hydroxyethyl)-6-(4-methyl-1-piperazinylmethyl)nicotinamide,
(9) N-(2-Hydroxyethyl)-6-(4-diphenylmethyl-1-piperazinylmethyl)nicotinamide,
(10) N-(3-Hydroxypropyl)-6-(4-methyl-1-piperazinyl)-nicotinamide,
(11) N-(2-Nitroxyethyl)-6-(4-methyl-1-piperazinyl)-nicotinamide,
(12) N-(2-Nitroxyethyl)-6-(4-methyl-1-piperazinyl)-nicotinamide dihydrochloride,
(13) N-(2-Nitroxyethyl)-6-(4-ethyl-1-piperazinyl)-nicotinamide dihydrochloride,
(14) N-(2-Nitroxyethyl)-6-(4-methyl-1-homopiperazinyl)nicotinamide dihydrochloride,
(15) N-(2-Nitroxyethyl)-6-(4-methyl-1-piperazinylmethyl)nicotinamide,
(16) N-(2-Nitroxyethyl)-6-(4-diphenylmethyl-1-piperazinylmethyl)nicotinamide,
(17) N-(2-Nitroxyethyl)-2-(4-methyl-1-piperazinyl)-nicotinamide,
(18) N-(2-Nitroxyethyl)-2-(4-methyl-1-piperazinyl)-nicotinamide dihydrochloride,
(19) N-(2-Nitroxyethyl)-6-(4-diphenylmethyl-1-piperazinyl)nicotinamide,
(20) N-(2-Nitroxyethyl)-6-(4-diphenylmethyl-1-piperazinyl)nicotinamide dihydrochloride,
(21) N-(3-Nitroxypropyl)-6-(4-methyl-1-piperazinyl)-nicotinamide,
(22) N-(3-Nitroxypropyl)-6-(4-methyl-1-piperazinyl)-nicotinamide dihydrochloride,
(23) N-(4-Hydroxybutyl)-6-(4-methyl-1-piperazinyl)-nicotinamide,
(24) N-(4-Nitroxybutyl)-6-(4-methyl-1-piperazinyl)-nicotinamide,
(25) N-(5-Hydroxypentyl)-6-(4-methyl-1-piperazinyl)-nicotinamide,
(26) N-(6-Hydroxyhexyl)-6-(4-methyl-1-piperazinyl)-nicotinamide,
(27) N-(8-Hydroxyoctyl)-6-(4-methyl-1-piperazinyl)-nicotinamide,
(28) 4-Hydroxy-1-[6-(4-methyl-1-piperazinyl)nicotinyl]-piperidine,
(29) N-(5-Nitroxypentyl)-6-(4-methyl-1-piperazinyl)-nicotinamide,
(30) N-(6-Nitroxyhexyl)-6-(4-methyl-1-piperazinyl)-nicotinamide,
(31) N-(8-Nitroxyoctyl)-6-(4-methyl-1-piperazinyl)-nicotinamide, and
(32) 1-[6-(4-methyl-1-piperazinyl)nicotinyl]-4-nitroxypiperidine.

The compounds of the invention can be prepared by reacting a compound of formula (II)

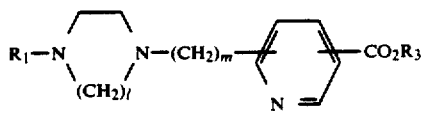
(II)

wherein $R_1$, l and m are as defined above and $R_3$ is hydrogen $C_1$-$C_6$ alkyl, with an amino compound of formula (III)

$$NH_2-(CH_2)_n-R_2 \quad (III)$$

wherein $R_2$ and n are as defined above and optionally subjecting the resulting reaction product where $R_2$ is OH to esterification with nitric acid to give a compound of formula (I)

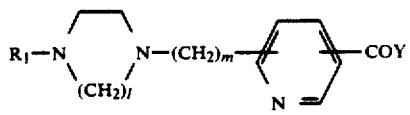
(I)

wherein $R_1$, Y, l and m are as defined above, or if necessary, converting the compound thus obtained to a physiologically acceptable acid addition salt.

Alternatively, the compounds of formula (I) wherein Y is $-NH(CH_2)_2-R_2$ ($R_2$ is OH or $-ONO_2$ and n is 5-8) and Y is

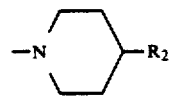

($R_2$ is OH or $-ONO_2$) can be prepared by reacting a compound of formula (IV)

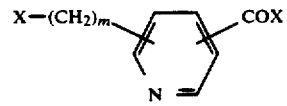
(IV)

wherein X is halogen and m is 0 or 1 with a compound of the formula $NH_2(CH_2)_nOH$ (n is 5-8) or

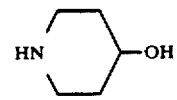

in an organic solvent to form a compound of the formula

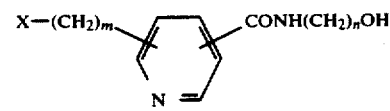

or

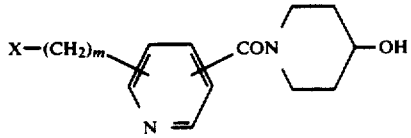

wherein X, m and n are as defined above and further condensing said compound with a compound of the formula

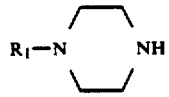

wherein $R_1$ is as defined above in the presence of an acid-binding agent to give a compound of formula (I) wherein Y is $-NH(CH_2)_n-OH$

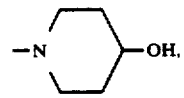

or esterifying the resulting compound to form a compound of formula (I) wherein Y is $-NH(CH_2)_n-ONO_2$ or

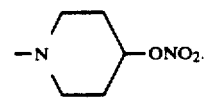

In case of using a compound of formula (II) wherein $R_3$ is $C_1$-$C_6$ alkyl, the reaction between a compound of formula (II) and a compound of formula (III) is effected using an excess amount of the compound of formula (III) with or without an organic solvent in the presence or absence of a catalyst such as 2-hydroxypyridine. The reaction is accomplished by stirring at a temperature between ordinary temperature and 150° C. for a period in the range from several tens minutes to several tens hours. Purification and isolation of the desired compounds are carried out by a conventional method. Thus a purified condensation product is obtained by extracting the reaction product with an organic solvent such as diethyl ether, ethyl acetate or dichloromethane, distilling off the extraction solvent from the extract and subjecting the residue to recrystallization or chromatography.

In cases where $R_2$ in the condensation product obtained is OH, a compound of formula (I) wherein $R_2$ is $ONO_2$ can be produced by dissolving or suspending said condensation product in an organic solvent, adding fuming nitric acid or a mixture of fuming nitric acid and acetic anhydride to the solution or suspension under ice-cooling and stirring the resulting mixture for 1-4 hours to form a nitrate ester.

In case of using a compound of formula (II) wherein $R_3$ is hydrogen, the compound (II) and an amino alcohol or its nitrate ester of formula (III) are subjected to condensation reaction in an organic solvent in the presence or absence of an appropriate amidating agent to form a compound of formula (I).

The reaction solvents used in these reactions include an aliphatic hydrocarbon such as n-hexane or petroleum ether; an aromatic hydrocarbon such as benzene, toluene or xylene; an alicyclic compound such as cyclohexane; a halogenated hydrocarbon such as carbon tetrachloride, chloroform, dichloroethane or trichloroethane; an aliphatic ketone such as acetone or methyl ethyl ketone; acetonitrile; N,N-dimethylformamide; dimethylsulfoxide or the like. Purification and isolation of the desired compounds are also carried out by a conventional method. Thus, a purified desired condensation product is obtained by distilling off the solvent after completion of the reaction, pouring the residue into an aqueous solution of sodium hydrogen carbonate, extracting the resulting mass with an organic solvent such as diethyl ether, ethyl acetate or dichloromethane, distilling off the extraction solvent from the extract and subjecting the residue to recrystallization or chromatography.

The compounds of formula (I) thus produced can be converted to acid addition salts thereof by a conventional method. The acid addition salts include acid addition salts of the compounds with an inorganic acid such as hydrochloric, sulfuric, phosphoric, hydrobromic or nitric acids, and acid addition salts of the compounds with an organic acid such as acetic, propionic, succinic, butyric, malic, citric, fumaric or tartaric acids.

The compound of formula (II) can be produced by condensing a compound of formula (V)

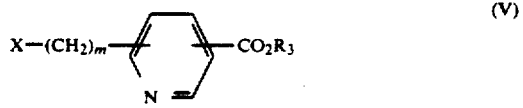

(V)

wherein X is halogen and $R_3$ is hydrogen or $C_1$–$C_6$ alkyl with a compound of formula (VI)

(VI)

wherein $R_1$ is hydrogen, $C_1$–$C_6$ alkyl, $C_3$–$C_6$ cycloalkyl or diphenylmethyl and l is 2 or 3 in the presence of an acid-binding agent. In cases where $R_1$ in a compound obtained by the condensation reaction is hydrogen, if necessary, the compound and a compound of the formula $R'_1$—X wherein $R'_1$ is $C_1$–$C_6$ alkyl and X is halogen may be reacted in an organic solvent in the presence of an acid-binding agent to give a compound of formula (II) wherein $R_1$ is $C_1$–$C_6$ alkyl. A compound of formula (II) wherein $R_1$ is hydrogen can be converted to a compound of formula (II) wherein $R_1$ is methyl by reaction with a mixture of formaldehyde and formic acid. The reaction can be accomplished under the reaction conditions described in Organic Synthesis Vol. 3, pages 723–725.

As clearly seen from the results of a pharmacological test shown below, the compounds of formula (I) of the invention exhibit marked blood flow-increasing and hypotensive actions in warm-blooded animals and can be used for the therapy or prevention of diseases in the cardiovascular system. Diseases in the cardiovascular system include disturbances of cerebral or peripheral circulation, ischemic heart diseases and hypertensions.

Thus, the invention further relates to pharmaceutical compositions for use in the therapy or prevention of the above-mentioned diseases, which comprise as an active ingredient a compound of formula (I) or a physiologically acceptable acid addition salt thereof.

The pharmaceutical compositions of the invention can orally or parenterally be administered in the suitable dosage forms. They can be administered alone, but are generally administered with a pharmaceutical carrier selected on the basis of the chosen route of administration and standard pharmaceutical practice. The dosage forms include tablets, capsules, suppositories, troches, syrups, creams, ointments, pasters, cataplasms, granules, powders, injections, suspensions and the like. Bi- or multi-layered tablets can also be prepared in combination with other drugs. Furthermore, tablets with conventional coating applied, for example, sugar-coated tablets, tablets with enteric coating or film-coated tablets can also be prepared.

In forming solid dosage forms there can be used additives such as lactose, white sugar, crystalline cellulose, corn starch, calcium phosphate, sorbitol, glycine, carboxymethyl cellulose, gum arabic, polyvinylpyrrolidone, hydroxypropyl cellulose, glycerin, polyethylene glycol, stearic acid, magnesium stearate and talc.

In forming semi-solid dosage forms, vegetable or synthetic waxes or fats and the like are used.

In forming liquid dosage forms, there can be employed additives such as an aqueous sodium chloride solution, sorbitol, glycerin, olive oil, almond oil, propylene glycol and ethyl alcohol.

The content of the active ingredient in the above dosage forms is in the range between 0.1 and 100% by weight, suitably between 1 and 50% by weight for oral administration and between 0.1 and 10% by weight for injection.

The dosage administered will, of course, vary depending upon the mode and route of administration, age, sex and weight of the patient, nature and extent of symptoms and the like. Usually a daily dosage of active ingredient can be about 1 to 1000 mg per kg of body weight.

The invention is further illustrated by the following non-limitative examples.

EXAMPLE 1

Preparation of N-(2-hydroxyethyl)-6-(4-methyl-1-piperazinyl)nicotinamide (compound 1)

A mixture of 3.29 g of methyl 6-(4-methyl-1-piperazinyl)nicotinate, 2.02 g of 2-aminoethanol and 1.00 g of 2-hydroxypyridine was heated to 120°–130° C. and stirred for 7 hours.

The resulting mixture was purified by column chromatography (silica gel; chloroform : methanol = 5 : 1) to give 3.02 g of N-(2-hydroxyethyl)-6-(4-methyl-1piperazinyl)nicotinamide (yield 94%).

EXAMPLES 2–10

The same procedure as in Example 1 was repeated but replacing methyl 6-(4-methyl-1-piperazinyl)nicotinate by methyl 6-(1-piperazinyl)nicotinate, methyl 6-(4-diphenylmethyl-1-piperazinyl)nicotinate, methyl 6-(4-ethyl-1-piperazinyl)nicotinate, methyl 6-(4-cyclopentyl1piperazinyl)nicotinate, methyl 6-(Methyl-1-homopiperazinyl)nicotinate, methyl 2-(4-methyl1piperazinyl)nicotinate, methyl 6-(4-methyl- 1piperazinyl)nicotinate, and methyl 6-(4-diphenylmethyl-1piperazinylmethyl)nicotinate, respectively to give N-(2-hydroxyethyl)-6-(1-piperazinyl)nicotinate (compound 2), N(2-hydroxyethyl)-6-(4-diphenylmethyl-1-piperazinyl)nicotinamide (compound 3), N-(2-hydroxyethyl)-6-(4-ethyl-1-piperazinyl)nicotinamide (compound 4), N-(2-hydroxyethyl)-6-(4-cyclopentyl-1-piperazinyl)nicotinamide (compound 5), N-(2-hydroxyethyl)-6-(4-methyl-1-homopiperazinyl)nicotinamide (compound 6), N-(2-hydroxyethyl)-2-(4-methyl-1-piperazinyl)nicotinamide (compound 7), N-(2-hydroxyethyl)-6-(4-methyl-1-piperazinylmethyl)nicotinamide (compound 8) and N-(2-hydroxyethyl)-6-(4-diphenylmethyl-1-piperazinylmethyl)nicotinamide (compound 9), respectively. Following the same procedure, replacement of 2-aminoethanol used in Example 1 by 3-aminopropanol gave N-(3-hydroxypropyl)-6-(4-methyl-1-piperazinyl)nicotinamide (compound 10).

EXAMPLES 11-12

Preparation of N-(2-hydroxyethyl)-6-(4-methyl-1-piperazinyl)nicotinamide (compound 11) and its dihydrochloride (compound 12)

To an ice-cooled solution of 11.00 g of the compound (obtained in Example 1) in 20 ml of methylene chloride was added dropwise 5 ml of fuming nitric acid while stirring below 0° C. The stirring was continued for 2 hours. The reaction mixture was poured into an aqueous sodium hydrogen carbonate solution and extracted with methylene chloride. The extract was washed twice with water and once with a saturated aqueous saline solution, dried over anhydrous magnesium sulfate and concentrated to afford N-(2-nitroxyethyl)-6-(4-methyl-1-piperazinyl)nicotinamide. The product was dissolved in ethanol and to the solution was added under ice-cooling hydrogen chloride-saturated ethanol. The hydrochloride thus formed was recrystallized from ethanol to give 0.54 g of N-(2-nitroxyethyl)-6-(4-methyl-1piperazinyl)-nicotinamide dihydrochloride (yield 34%).

EXAMPLES 13-16

The same procedures as above were repeated but replacing compound 1 by compounds 4, 6, 8 and 9, respectively to prepare N-(2-nitroxyethyl)-6-(4-ethyl-1-piperazinyl)-nicotinamide dihydrochloride (compound 13), N-2-nitroxyethyl)-6-(4-methyl-1-homopiperazinyl)-nicotinamide dihydrochloride (compound 14), N-(2-nitroxyethyl)-6-(4-methyl-1-piperazinylmethyl)-nicotinamide (compound 15) and N-2-nitroxyethyl)-6-(4-diphenylmethyl-1-piperazinylmethyl)nicotinamide (compound 16), respectively.

EXAMPLES 17-18

Preparation of N-(2-nitroxyethyl)-2-(4-methyl-1-piperazinyl)nicotinamide (compound 17) and its dihydrochloride (compound 18).

To a solution of 1.27 g of compound 7 prepared in Examples 2-10 in 13 ml of acetonitrile was added dropwise a mixture of 2.0 g of fuming nitric acid and 1.4 g of acetic anhydride while maintaining the temperature below −10° C. The mixture was stirred for 4 hours, then poured into an aqueous sodium hydrogen carbonate solution and extracted with methylene chloride. The extract was washed twice with water and once with a saturated aqueous saline solution, dried over anhydrous magnesium sulfate and concentrated to give N-(2-nitroxyethyl)-2-(4-methyl-1-piperazinyl)nicotinamide (compound 17). The product was dissolved in ethanol, and to the solution was added under ice-cooling hydrogen chloride-saturated ethanol. The hydrochloride thus formed was recrystallized from ethanol to give 1.32 g of N-(2-nitroxyethyl)-2-(4-methyl-1-piperazinyl) nicotinamide dihydrochloride (compound 18)(yield 66%).

EXAMPLES 19-22

The same procedures as above were repeated but replacing compound 7 by compounds 3 and 10, respectively to prepare N-(2-nitroxyethyl)-6-(4-diphenylmethyl-1-piperazinyl)nicotinamide (compound 19) and its dihydrochloride (compound 20), N-(3-nitroxypropyl)-6-(4-methyl-1-piperazinyl)nicotinamide (compound 21) and its dihydrochloride (compound 22).

EXAMPLE 23

Preparation of N-(4-hydroxybutyl)-6-(4-methyl-1-piperazinyl)nicotinamide (compound 23)

The same procedure as in Example 1 was repeated but replacing 2-aminoethanol by 4-aminobutanol to afford N-(4-hydroxybutyl)-6-(4-methyl-1-piperazinyl) nicotinamide.

EXAMPLE 24

The compound obtained in Example 23 was esterified in the same way as in Example 17 to give N-(4-nitroxybutyl)-6-(4-methyl-1-piperazinyl)nicotinamide (compound 24).

EXAMPLE 25

Preparation of N-(5-hydroxypentyl)-6-(4-methyl-1-piperazinyl)-nicotinamide (compound 25)

To 7.88 g of 6-chloronicotinic acid were added 7.3 ml of thionyl chloride and a few drops of DMF. The mixture was heated under reflux for 2 hours, and then the excess of thionyl chloride was distilled off to give crystals of 6-chloronicotinoyl chloride. A solution of the crystals in 60 ml of tetrahydrofuran was added dropwise to a solution of 15.47 g of 5-aminopentanol in 200 ml of tetrahydrofuran at a temperature below 0° C. The mixture was stirred overnight while gradually raising the temperature to room temperature. The solvent was distilled off and to the residue was added water followed by extraction with ethyl acetate. Then, the extract was washed successively with water and a saturated brine solution, dried over magnesium sulfate. The solvent was distilled off and the residue was recrystallized from ethyl acetate to give 11.24 g of N-(5-hydroxypentyl)-6-chloronicotinamide (yield 93%).

To a solution of 4.13 g of the amide obtained above, 8.51 g of 1-methylpiperazine and 1.72 g of diisopropylamine in 80 ml of p-xylene was added a catalytic amount of NaI, and the mixture was heated to 120°-130° C. and stirred for 4 hours. The reaction mixture was poured into water and extracted with chloroform. The extract was washed successively with water and a saturated brine solution, then dried over anhydrous magnesium sulfate and concentrated. The concentrate was purified by column chromatography (silica gel, chloroform : methanol=4 : 1) to give 4.65 g of N-(5-hydroxypentyl)-6-(4-methyl-1-piperazinyl)nicotinamide (yield 89%).

EXAMPLES 26-28

The same procedure as in Example 25 was repeated but replacing 5-aminopentanol by 6-aminohexanol, 8-aminooctanol and 4-hydroxypiperidine, respectively to give N-(6-hydroxyhexyl)-6-(4-methyl-1-piperazinyl)-nicotinamide (compound 26), N-(8-hydroxyoctyl)-6-(4-methyl-1-piperazinyl)nicotinamide (compound 27) and 4-hydroxy-1-[6-(4-methyl-1-piperazinyl)nicotinyl]-piperidine (compound 28), respectively.

EXAMPLES 29-32

The compounds produced in Examples 26-28 were esterified in the same manner as in Example 17 to prepare N-(5-nitroxypentyl)-6-(4-methyl-1-piperazinyl) nicotinamide (compound 29), N-(6-nitroxyhexyl)-6-(4-methyl-1-piperazinyl)nicotinamide (compound 30), N-(8-nitroxyoctyl)-6-(4-methyl-1-piperazinyl)nicotinamide (compound 31) and 1-[6-(4-methyl-1-piperazinyl)-nicotinyl]-4-nitroxypiperidine (compound 32), respectively.

Table 1 shows compounds 1-32 prepared as above for chemical structure, yield and physical properties.

TABLE 1

| Compound No. | Structure | Yield | m.p. (°C) (Solvent for recrystallization) | IR ν$_{max}$ (cm$^{-1}$) | $^1$H-NMR |
|---|---|---|---|---|---|
| 1 | CH₃N-piperidine-pyridine-CONH(CH₂)₂OH | 94% | 112–114 (Ethyl acetate) | (KBr) 3414, 3362, 1608, 1507, 1247 | (CDCl₃) δ8.59(1H, d, J=2.4Hz), 7.89(1H, dd, J=9.0, 2.4Hz), 6.57(1H, d, J=9.0Hz), 3.79(2H, t, J=4.4Hz), 3.73–3.49(6H, m), 2.49(4H, t, J=5.0Hz), 2.34(3H, s) |
| 2 | HN-piperidine-pyridine-CONH(CH₂)₂OH | 69% | 140–142 | (KBr) 3265, 2920, 2855, 2830, 1640, 1600, 1500 | (DMSO-d₆) δ8.59(1H, d, J=2.2Hz), 8.26–8.24(1H, m), 7.94(1H, dd, J=8.8, 2.2Hz), 6.78(1H, d, J=8.8Hz), 4.82–4.58(1H, m), 3.60–3.20(8H, m), 2.82–2.18(4H, m) |
| 3 | C₆H₅-CH(C₆H₅)-N-piperazine-pyridine-CONH(CH₂)₂OH | 78% | 190–192 (Acetonitrile) | (KBr) 3328, 2850, 1632, 1612, 1501, 1245 | (DMSO-d₆) δ8.58(1H, s), 8.26–8.16(1H, m), 7.94(1H, d, J=8.9Hz), 7.52–7.13(10H, m), 6.77(1H, d, J=8.9Hz), 4.70(1H, t, J=5.3Hz), 4.32(1H, s), 3.66–3.40(6H, m), 3.77–3.24(2H, m), 2.46–2.32(4H, m) |
| 4 | C₂H₅N-piperazine-pyridine-CONH(CH₂)₂OH | 95% | 125–126 (Ethyl acetate) | (KBr) 3372, 3270, 2928, 2836, 1630, 1608, 1539, 1299, 778 | (CDCl₃) δ8.59(1H, d, J=2.4Hz), 7.89(1H, dd, J=9.0, 2.4Hz), 6.90–6.78(1H, m), 6.58(1H, d, J=9.0Hz), 3.65(2H, t, J=5.1Hz), 3.71–3.51(2H, m), 3.65(4H, t, J=5.1Hz), 2.53(4H, t, J=5.1Hz), 2.46(2H, q, J=7.2Hz), 1.13(3H, t, J=7.2Hz) |
| 5 | cyclopentyl-N-piperazine-pyridine-CONH(CH₂)₂OH | 72% | 171–174 (Acetonitrile/Ethyl acetate) | (KBr) 3380, 2970, 2870, 1641, 1602, 1537, 1496, 1247 | (CDCl₃) δ8.57(1H, d, J=2.4Hz), 7.89(1H, dd, J=9.0, 2.4Hz), 6.60(1H, d, J=9.0Hz), 6.60–6.46(1H, m), 3.82(2H, t, J=5.1Hz), 3.75–3.55(6H, m), 2.78–2.43(5H, m), 1.99–1.32(10H, m) |
| 6 | CH₃N-homopiperazine-pyridine-CONH(CH₂)₂OH | 94% | Oily product | (Film) 2944, 2796, 1713, 1605, 1437, 1368, 782 | (CDCl₃) δ8.78(1H, d, J=2.4Hz), 7.99(1H, dd, J=9.0, 2.4Hz), 6.46(1H, d, J=9.0Hz), 3.97–3.83(2H, m), 3.86(3H, s), 3.70(2H, t, J=6.4Hz), 2.75–2.66(2H, m), 2.61–2.52(2H, m), 2.38(3H, s), 2.10–1.96(2H, m) |
| 7 | pyridine-CONH(CH₂)₂OH with piperidine-NCH₃ | 73% | 123–125 (Ethyl acetate) | (KBr) 3316, 3260, 1644, 1544, 1427 | (CDCl₃) δ9.14–9.02(1H, m), 8.34(1H, dd, J=4.9, 2.0Hz), 8.28(1H, dd, J=7.7, 2.0), 7.08(1H, dd, J=7.7, 4.9Hz), 3.48(2H, t, J=4.9Hz), 3.70–3.58(2H, m), 3.25(4H, t, J=4.9Hz), 2.60(4H, t, J=4.9Hz), 2.36(3H, s) |

TABLE 1-continued

| Compound No. | Structure | Yield | m.p. (°C.) (Solvent for recrystallization) | IR ν$_{max}$ (cm$^{-1}$) | 1H-NMR |
|---|---|---|---|---|---|
| 8 | CH$_3$N-[piperidine]-N-CH$_2$-[pyridine]-CONH(CH$_2$)$_2$OH | 84% | Oily product | (Film) 3290, 3075, 2930, 2800, 1640, 1595, 1545 | (CDCl$_3$)δ8.94(1H, d, J=2.2Hz), 8.10(1H, dd, J=8.1, 2.2Hz), 7.49(1H, d, J=8.1Hz), 7.28-7.02(1H, m), 3.83(2H, t, J=4.9Hz), 3.70 (2H, s), 3.64(2H, t, J=4.9Hz), 2.67-2.39(8H, m), 2.31(3H, s) |
| 9 | C$_6$H$_5$-CH(C$_6$H$_5$)-N-[piperidine]-N-CH$_2$-[pyridine]-CONH(CH$_2$)$_2$OH | 95% | Oily product | (Film) 3280, 3080, 2940, 2810, 1650, 1600, 1490 | (CDCl$_3$)δ8.93(1H, d, J=2.2Hz), 8.05(1H, dd, J=8.3, 2.2Hz), 7.52-7.10(10H, m), 6.57(1H, d, J=8.3Hz), 6.32-6.23(1H, m), 4.23(1H, s), 3.82(2H, t, J=5.0Hz), 3.67(2H, s), 3.62(2H, t, J=5.0Hz), 2.62-2.34(8H, m) |
| 10 | CH$_3$N-[piperidine]-N-[pyridine]-CONH(CH$_2$)$_3$OH | 88% | 123-125 (Ethyl acetate) | (KBr) 3310, 2938, 2846, 1623, 1604, 1545 | (CDCl$_3$)δ8.56(1H, d, J=2.4Hz), 7.90(1H, dd, J=9.0, 2.4Hz), 6.68-6.70(1H, m), 6.61(1H, d, J=9.0Hz), 3.80-3.53(9H, m), 2.50 (4H, t, J=5.0Hz), 2.34(3H, s), 1.86-1.71(2H, m) |
| 11 | CH$_3$N-[piperidine]-N-[pyridine]-CONH(CH$_2$)$_2$ONO$_2$ | 70% | 95-97 (Hexane-acetone) | (KBr) 3280, 2930, 2790, 1635, 1605, 1540, 1500, 1275 | (CDCl$_3$)δ8.57(1H, d, J=1.9Hz), 7.88(1H, dd, J=9.3, 1.9Hz), 6.62(1H, d, J=9.3Hz), 6.49-6.25(1H, m), 4.65(2H, t, J=5.1Hz), 3.08(2H, dt, J=5.0, 5.0), 3.68(4H, t, J=5.1Hz), 2.51(4H, t, J=5.1Hz), 2.35(3H, s) |
| 12 | CH$_3$N-[piperidine]-N-[pyridine]-CONH(CH$_2$)$_2$ONO$_2$·2HCl | 34% | 143-145 (Dec.) (Ethanol) | (KBr) 3244, 2926, 1667, 1647, 1609, 1545, 1279 | (CD$_3$OD)δ8.56(1H, d, J=2.2Hz), 8.46(1H, dd, J=9.5, 2.2Hz), 7.50(1H, d, J=9.5Hz), 4.68(2H, t, J=5.4Hz), 4.68-4.47(2H, m), 3.85-3.10(7H, m), 3.48-3.28(2H, m), 3.00(3H, s) |
| 13 | C$_2$H$_5$N-[piperidine]-N-[pyridine]-CONH(CH$_2$)$_2$ONO$_2$·2HCl | 39% | 163-164 (Dec.) (Ethanol) | (KBr) 3292, 2782, 1676, 1657, 1641, 1541, 1282 | (CD$_3$OD)δ8.55(1H, d, J=2.2Hz), 8.41(1H, dd, J=9.5, 2.2Hz), 7.47(1H, d, J=9.5Hz), 4.67(2H, t, J=5.4Hz), 4.67-4.47(2H, m), 3.88-3.60(7H, m), 3.42-3.18(6H, m), 1.43(3H, t, J=7.3Hz) |
| 14 | CH$_3$N-[piperidine]-N-[pyridine]-CONH(CH$_2$)$_2$ONO$_2$·2HCl | 12% | 132-134 (Dec.) (Ethanol) | (KBr) 3244, 2948, 2700, 1670, 1637, 1608, 1541, 1281, 761 | (CD$_3$OD)δ8.51(1H, d, J=2.4Hz), 8.43(1H, dd, J=9.5, 2.4Hz), 7.46(1H, d, J=9.5Hz), 4.68(2H, t, J=5.2Hz), 4.36-4.05(2H, m), 4.00-3.60(7H, m), 3.57-3.36(2H, m), 2.98(3H, s), 2.63-2.32(2H, m) |
| 15 | CH$_3$N-[piperidine]-N-CH$_2$-[pyridine]-CONH(CH$_2$)$_2$ONO$_2$ | 72% | Oily product | (Film) 3300, 2945, 2800, 1640, 1600, 1545, 1280 | (CDCl$_3$)δ8.94(1H, d, J=2.2Hz), 8.09(1H, dd, J=8.3, 2.2Hz), 7.53(1H, d, J=8.3Hz), 6.79-6.68(1H, m), 4.68(2H, t, J=5.1Hz), 3.84(2H, dt, J=5.6, 5.1Hz), 3.72(2H, s), 2.67-2.42(8H, m), 2.32(3H, s) |

TABLE 1-continued

| Compound No. | Structure | Yield | m.p. (°C) (Solvent for recrystallization) | IR ν_max (cm⁻¹) | ¹H-NMR |
|---|---|---|---|---|---|
| 16 | 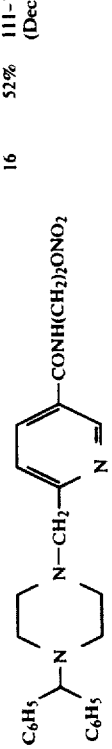 | 52% | 111-112 (Dec.) | (KBr) 3060, 3020, 2930, 2805, 1635, 1595, 1275 | (CDCl₃)δ8.93(1H, d, J=2.2Hz), 8.07(1H, dd, J=8.4, 2.2Hz), 7.59-7.11(12H, m), 6.83-6.70(1H, m), 4.66(2H, t, J=5.0Hz), 4.25(1H, s), 3.89-3.71(4H, m), 2.69-2.33(8H, m) |
| 17 | 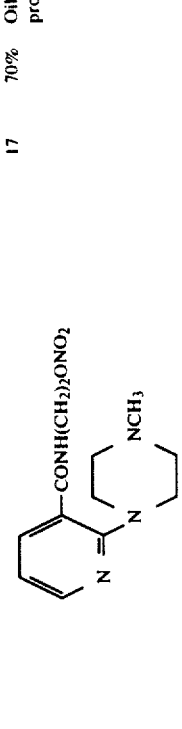 | 70% | Oily product | (Film) 3248, 2942, 2850, 2810, 1636, 1279 | CDCl₃)δ9.41-9.26(1H, m), 8.41(1H, dd, J=4.9, 2.0Hz), 8.33(1H, dd, J=7.8, 2.0Hz), 7.13(1H, dd, J=7.8, 4.9Hz), 4.69(2H, t, J=4.9Hz), 3.90-3.77(2H, m), 3.23(4H, t, J=4.9Hz), 2.61(4H, t, J=4.9Hz), 2.38, (3H, s) |
| 18 | 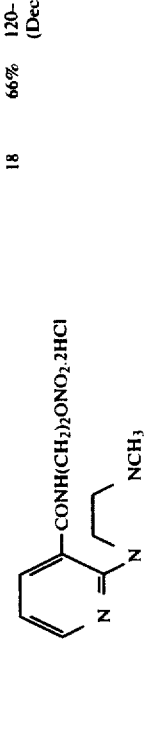 | 66% | 120-122 (Dec.) | (KBr) 3422, 1662, 1634, 1620, 1386, 1281 | (CD₃OD)δ8.30(1H, dd, J=5.9, 2.0Hz), 8.22(1H, dd, J=7.6, 2.0Hz), 7.31(1H, dd, J=7.6, 5.9Hz), 4.71(2H, t, J=5.0Hz), 4.08-3.89(2H, m), 3.79(2H, t, J=5.0Hz), 3.74-3.53(5H, m)3.47-3.30(2H, m), 3.00(3H, s) |
| 19 | 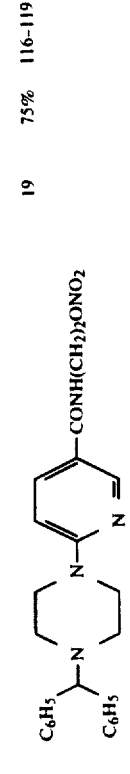 | 75% | 116-119 | (KBr) 3020, 2955, 2915, 2845, 2805, 1635, 1600, 1495, 1275 | (CDCl₃)δ8.85(1H, d, J=2.2Hz), 7.86(1H, dd, J=9.0, 2.2Hz), 7.53-7.16(10H, m), 6.57(1H, d, J=9.0Hz), 6.49-6.35(1H, m), 4.63(2H, t, J=5.1Hz), 4.31(1H, s), 3.78(2H, dt, J=5.1, 5.1Hz), 3.72-3.59(4H, m, 2.64-2.47(4H, m) |
| 20 | 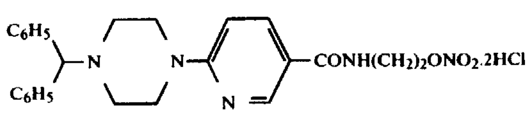 | 72% | 120-121 (Dec.) (Ethyl acetate-ethyl alcohol) | (KBr) 3120, 2574, 1636, 1605, 1280 | (CD₃OD)δ8.55(1H, d, J=2.2Hz), 8.49(1H, dd, J=8.3, 2.2Hz), 7.93-7.82(4H, m), 7.57-7.37(7H, m), 5.62(1H, s), 4.67(2H, t, J=5.1 Hz), 4.48-4.02(4H, m), 3.73(2H, m), 3.58-3.43(4H, m) |
| 21 | 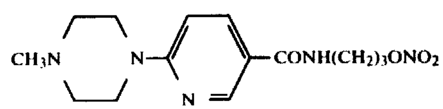 | 90% | 108-110 (Dec.) | (KBr) 3262, 2946, 2848, 1625, 1603, 1283 | (CDCl₃)δ8.55(1H, d, J=2.4Hz), 7.89(1H, dd, J=9.2, 2.4Hz), 6.63(1H, d, J=9.2Hz), 6.22-6.09(1H, m), 4.57(2H, t, J=6.0Hz), 3.68 (2H, t, J=5.3Hz), 3.63-3.49(2H, m), 2.51(4H, t, J=5.3Hz), 2.35(3H, s), 2.16-2.5(2H, m) |
| 22 | 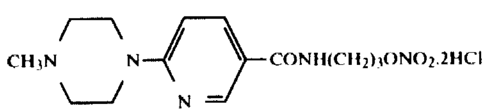 | 79% | 139-141 (Dec.) (Ethyl alcohol-methyl alcohol) | (KBr) 3294, 2868, 2684, 1663, 1645, 1618, 1545, 1279 | (CD₃OD)δ8.55(1H, d, J=2.4Hz), 8.46(1H, dd, J=9.5, 2.4Hz), 7.53(1H, d, J=9.5Hz), 4.67-4.45(4H, m), 3.89-3.60(4H, m), 3.56-3.32(5H, m), 3.01(3H, s), 2.12-1.94(2H, m) |

TABLE 1-continued

| Compound No. | Structure | Yield | m.p. (°C.) (Solvent for recrystallization) | IR ν_max (cm$^{-1}$) | $^1$H-NMR |
|---|---|---|---|---|---|
| 23 | [pyridine with CH$_3$N-piperazine and CONH(CH$_2$)$_4$OH] | 49% | Amorphous | (KBr) 3325, 2940, 1630, 1610, 1500, 1260 | (CDCl$_3$)δ8.56(1H, d, J=2.5Hz), 7.91(1H, dd, J=9.0, 2.5Hz), 6.61(1H, d, J=9.0Hz), 6.54(1H, m), 3.71(2H, t, J=5.8Hz), 3.65(4H, t, J=5.4Hz), 3.47(2H, m), 2.50(4H, t, J=5.0Hz), 2.34(3H, s), 1.68 (4H, m) |
| 24 | [pyridine with CH$_3$N-piperazine and CONH(CH$_2$)$_4$ONO$_2$] | 57% | Colorless crystal 77–80 | (KBr) 3300, 1640, 1600, 1500, 1250 | (CDCl$_3$)δ8.53(1H, d, J=2.3Hz), 7.89(1H, dd, J=9.3, 2.3Hz), 6.62(1H, d, J=9.3Hz), 6.13(1H, m), 4.51(2H, t, J=5.9Hz), 3.67(4H, t, J=5.1Hz), 3.48(2H, m), 2.50(4H, t, J=5.2Hz), 2.38(3H, s), 1.97–1.62(4H, m) |
| 25 | [pyridine with CH$_3$N-piperazine and CONH(CH$_2$)$_5$OH] | 89% | Amorphous | (KBr) 3400, 2950, 1640, 1600, 1500, 1260 | (CDCl$_3$)δ8.55(1H, d, J=2.5Hz), 7.90(1H, dd, J=9.2, 2.5Hz), 6.62(1H, d, J=8.7Hz), 6.20(1H, m), 3.66(6H, m), 3.44(2H, m), 2.50 (4H, t, J=5.3Hz), 2.34(3H, s), 1.78–1.45(6H, m) |
| 26 | [pyridine with CH$_3$N-piperazine and CONH(CH$_2$)$_5$OH] | 80% | Amorphous | (KBr) 3400, 2950, 1615, 1605, 1500, 1260 | (CDCl$_3$)δ8.54(1H, s), 7.89(1H, d, J=9.0Hz), 6.60(1H, d, J=9.0Hz), 6.25(1H, m), 3.61(6H, m), 3.39(2H, m), 2.48(4H, t, J=4.9Hz), 2.33(3H, s), 1.65–1.29(8H, m) |
| 27 | [pyridine with CH$_3$N-piperazine and CONH(CH$_2$)$_8$OH] | 77% | Amorphous | (KBr) 3300, 2950, 1630, 1610, 1500, 1250 | (CDCl$_3$)δ8.55(1H, d, J=2.9Hz), 7.91(1H, dd, J=8.6, 2.9Hz), 6.62(1H, d, J=8.6Hz), 6.11(1H, m), 3.61(6H, m), 3.44(2H, m), 2.50 (4H, t, J=5.1Hz), 2.32(3H, s), 1.66–1.12(12H, m) |
| 28 | [pyridine with CH$_3$N-piperazine and CON-cyclohexyl-OH] | 82% | Colorless crystal 140–143 | (KBr) 3500, 3350, 1610, 1440, 1260, 1100 | (CDCl$_3$)δ8.27(1H, d, J=2.3Hz), 7.61(1H, dd, J=9.7, 2.3Hz), 6.62(1H, d, J=9.7Hz), 3.96(1H, m), 3.63(4H, t, J=5.7Hz), 3.31(2H, m), 2.51(4H, t, J=5.7Hz), 2.48(3H, s), 2.15–1.43(6H, m) |
| 29 | [pyridine with CH$_3$N-piperazine and CONH(CH$_2$)$_5$ONO$_2$] | 68% | Colorless crystal 100–103 | (KBr) 3300, 1630, 1610, 1290, 1250 | (CDCl$_3$)δ8.55(1H, d, J=1.9Hz), 7.90(1H, dd, J=8.8, 2.4Hz), 6.63(1H, d, J=8.8Hz), 6.01(1H, m), 4.46(2H, t, J=6.3Hz), 3.67(4H, t, J=4.9Hz), 3.47(2H, m), 2.50(4H, t, J=5.3Hz), 2.33(3H, s), 1.85–1.40(6H, m) |
| 30 | [pyridine with CH$_3$N-piperazine and CONH(CH$_2$)$_6$ONO$_2$] | 60% | Colorless crystal 67–69 | (KBr) 3300, 1620, 1600, 1280, 1250 | (CDCl$_3$)δ8.53(1H, d, J=2.9Hz), 7.89(1H, dd, J=8.6, 2.9Hz), 6.62(1H, d, J=8.6Hz), 5.97(1H, m), 4.43(2H, t, J=5.7Hz), 3.67(4H, t, J=5.7Hz), 3.44(2H, m), 2.50(4H, t, J=5.7Hz), 2.33(3H, s), 1.80–1.30(8H, m) |

TABLE 1-continued

| Compound No. | Structure | Yield | m.p. (°C.) (Solvent for recrystallization) | IR ν$_{max}$ (cm$^{-1}$) | $^1$H-NMR |
|---|---|---|---|---|---|
| 31 | CH$_3$N⟨piperazine⟩-pyridine-CONH(CH$_2$)$_8$ONO$_2$ | 76% | Colorless crystal 70-72 | (KBr) 3400, 1630, 1600, 1240 | (CDCl$_3$)δ8.53(1H, d, J=2.5Hz), 7.92(1H, dd, J=9.1, 2.9Hz), 6.64(1H, d, J=9.0Hz), 6.00(1H, m), 4.43(2H, t, J=6.3Hz), 3.66(4H, t, J=5.7Hz), 3.41(2H, m), 2.50(4H, t, J=5.7Hz), 2.35(3H, s), 1.80-1.20(12H, m) |
| 32 | CH$_3$N⟨piperazine⟩-pyridine-CON⟨piperidine⟩-ONO$_2$ | 67% | Colorless crystal 93-96 | (KBr) 3400, 1620, 1600, 1440, 1240, 870 | (CDCl$_3$)δ8.26(1H, d, J=2.9Hz), 7.61(1H, dd, J=9.7, 2.9Hz), 6.63(1H, d, J=9.7Hz), 5.20(1H, m), 3.90(2H, m), 3.64(4H, t, J=5.7Hz), 3.60(2H, m), 2.51(4H, t, J=5.7Hz), 2.35(3H, s), 2.05(2H, m), 1.85(2H, m) |

Blood flow-increasing and hypotensive actions were evaluated for the representative compounds of the invention by the method as described below.

EXPERIMENTAL METHOD

Blood flow was measured unbloodily by means of an electromagnetic blood flow meter for right vertebral artery, right common carotid artery and left femoral artery of the pentobarbital-anesthesized dog. Mean blood pressure was measured from a cannula in a femoral artery with a blood pressure transducer. The test compound was solved in saline and was intravenously administered at a dose of 1 mg/kg. Results of the test were expressed in terms of the percentage of post-administration change from the value prior to administration of a test compound.

Results of the measurement are shown in Table 2 below.

TABLE 2

| Compound No. | Percent (%) Increase in Blood Flow | | | Percent (%) Decrease in Mean Blood Pressure |
|---|---|---|---|---|
| | Vertebral artery | Common carotid artery | Femoral artery | |
| 2 | +10 | +41 | — | — |
| 12 | +137 | +55 | +80 | −10 |
| 13 | +158 | +50 | +95 | −16 |
| 14 | +69 | +18 | +22 | −9 |
| 18 | +56 | +9 | +46 | −10 |
| 20 | +36 | +11 | +2 | −2 |
| 22 | +140 | +30 | +97 | −12 |
| 24 | +80 | +50 | — | −17 |
| 29 | +106 | +113 | — | −25 |
| 30 | +97 | +100 | — | −37 |

Useful pharmaceutical dosage-forms for administration of the compounds of this invention are illustrated below.

| Tablets (per tablet) | |
|---|---|
| N-(2-Nitroxyethyl)-6-(4-methyl-1-piperazinyl)nicotinamide | 10 mg |
| Lactose | 67 mg |
| Crystalline cellulose | 15 mg |
| Corn starch | 7 mg |
| Magnesium stearate | 1 mg |
| | 100 mg |

The components were uniformly blended to prepare powders for direct tableting. The powders were formed by means of a rotary tableting machine to tablets 6 mm in diameter each weighing 100 mg.

| Granules (per pack) | | |
|---|---|---|
| N-(2-Nitroxyethyl)-6-(4-methyl-1-piperazinyl)nicotinamide | 10 mg | |
| Lactose | 90 mg | A |
| Corn starch | 50 mg | |
| Crystalline cellulose | 50 mg | |
| Hydroxypropyl cellulose | 10 mg | B |
| Ethanol | 90 mg | |

Component A was uniformly blended, to which was added solution B. The mixture was kneaded. The kneaded mass was graded by the extrusion granulating method and then dried in a drier at 50° C. The dried granules were screened to a mesh range between 297 μm and 1460 μm to prepare granules. One pack weighed 200 mg.

| Syrups | |
|---|---|
| N-(2-Nitroxyethyl)-6-(4-methyl-1-piperazinyl)nicotinamide | 1.000 g |
| White sugar | 30.000 g |
| D-Sorbitol 70 w/v % | 25.000 g |
| Ethyl paraoxybenzoate | 0.030 g |
| Propyl paraoxybenzoate | 0.025 g |
| Flavors | 0.200 g |
| Glycerin | 0.150 g |
| 96% Ethanol | 0.500 g |
| Distilled water | q.s. |
| | Total to 100 ml |

White sugar, D-sorbitol, methyl paraoxybenzoate, propyl paraoxybenzoate and the active ingredient were dissolved in 60 g of warm water. After cooling, a solution of the flavors in the glycerin and the ethanol was added. To the resulting mixture was added the water to 100 ml.

| Injections | |
|---|---|
| N-(2-Nitroxyethyl)-6-(4-methyl-1-piperazinyl)nicotinamide | 1 mg |
| Sodium chloride | 10 mg |
| Distilled water | q.s. |
| | Total to 1.0 ml |

Sodium chloride and the active ingredient were dissolved in distilled water to a total volume of 1.0 ml.

| Suppositories | |
|---|---|
| N-(2-Nitroxyethyl)-6-(4-methyl-1-piperazinyl)nicotinamide | 2 g |
| Polyethylene glycol 4000 | 20 g |
| Glycerin | 78 g |
| | Total to 100 g |

The active ingredient was dissolved in the glycerin. To the solution was added polyethylene glycol 4000 and the mixture was dissolved under heat. The solution was poured into a suppository mold to prepare suppositories each weighing 1.5 g.

What is claimed is:

1. A compound of formula (I)

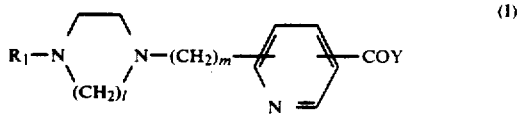

wherein $R_1$ is hydrogen; $C_1$-$C_6$ alkyl; $C_3$-$C_6$ cycloalkyl or diphenylmethyl;

Y is $-NH(CH_2)_n-R_2$ or

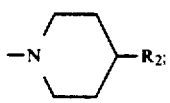

$R_2$ is OH or $-ONO_2$;

l is 2 or 3; m is 0 or 1; and n is 2 to 8; and physiologically acceptable acid addition salts thereof, provided that $-COY$ is in the 3- position of the pyridine ring.

2. A compound of claim 1 wherein $R_1$ is methyl, ethyl, n-propyl, i-propyl, n-butyl, i-butyl, tert-butyl, hexyl, cyclopentyl or cyclohexyl.

3. A compound of claim 1 wherein Y is $-NH(CH_2)_n-R_2$, $R_2$ is OH or $-ONO_2$ and n is 2 to 8.

4. A compound of claim 1 wherein Y is

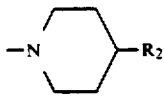

and $R_2$ is OH or $-NO_2$.

5. A pharmaceutical composition having blood flow-increasing and hypotensive actions which comprises a therapeutically effective amount of a compound of claim 1 or physiologically acceptable addition salts thereof and a pharmaceutically acceptable carrier.

6. A pharmaceutical composition having blood flow-increasing and hypotensive actions which comprises a therapeutically effective amount of a compound of claim 2 or physiologically acceptable addition salts thereof and a pharmaceutically acceptable carrier.

7. A pharmaceutical composition having blood flow-increasing and hypotensive actions which comprises a therapeutically effective amount of a compound of claim 3 or physiologically acceptable addition salts thereof and a pharmaceutically acceptable carrier.

8. A pharmaceutical composition having blood flow-increasing and hypotensive actions which comprises a therapeutically effective amount of a compound of claim 4 or physiologically acceptable addition salts thereof and a pharmaceutically acceptable carrier.

* * * * *